United States Patent
Knierbein

(10) Patent No.: US 6,709,424 B1
(45) Date of Patent: Mar. 23, 2004

(54) CONNECTOR WITH A COUPLING SYSTEM AND A PORT SYSTEM

(75) Inventor: Bernd Knierbein, Neu-Anspach (DE)

(73) Assignee: Fresnius Kabi Deutschland GmbH, Bad Homburg v.d.H. (DE)

( * ) Notice: Subject to any disclaimer, the term of this patent is extended or adjusted under 35 U.S.C. 154(b) by 305 days.

(21) Appl. No.: 09/594,953

(22) Filed: Jun. 15, 2000

(30) Foreign Application Priority Data

Jun. 16, 1999 (DE) ......................................... 199 27 356

(51) Int. Cl.⁷ ........................... A61M 5/32; A61M 39/10
(52) U.S. Cl. ........................ 604/411; 604/414; 604/533
(58) Field of Search ............................... 604/249, 256, 604/263, 533, 534, 536, 539, 905, 411, 412, 414

(56) References Cited

U.S. PATENT DOCUMENTS

| | | | | |
|---|---|---|---|---|
| 4,432,764 A | * | 2/1984 | Lopez | 604/533 |
| 4,564,054 A | | 1/1986 | Gustavsson | 141/329 |
| 4,898,209 A | | 2/1990 | Zbed | 137/614.04 |
| 5,957,898 A | * | 9/1999 | Jepson et al. | 128/912 |
| 6,050,978 A | * | 4/2000 | Orr et al. | 251/149.1 |
| 6,258,078 B1 | * | 7/2001 | Thilly | 206/363 |
| 6,290,688 B1 | * | 9/2001 | Lopez et al. | 604/500 |

FOREIGN PATENT DOCUMENTS

| | | | |
|---|---|---|---|
| EP | 0 499 764 A1 | 8/1992 | A61J/1/20 |
| WO | WO 93/20772 | 10/1993 | A61B/19/00 |
| WO | WO 98/48765 | 11/1998 | A61J/1/05 |

* cited by examiner

Primary Examiner—Angela D. Sykes
Assistant Examiner—Leslie R Deak
(74) Attorney, Agent, or Firm—Heslin Rothenberg Farley & Mesiti P.C.

(57) ABSTRACT

A connector system consists of a coupling system and a port system for coupling a flexible tubing system to a container containing medicinal fluids. The coupling system includes a spike to which the flexible tubing system can be connected and a sheath enveloping the spike over its entire length. The spike sheath consists of two parts that can be screwed together for telescopic elongation or shortening. For connection of the coupling system to the port system, the spike sheath is connected to the port system. Then the first part is screwed onto the second part completely, whereby the spike advances and pierces a diaphragm of the port system.

10 Claims, 4 Drawing Sheets

CONNECTOR WITH A COUPLING SYSTEM AND A PORT SYSTEM

BACKGROUND OF THE INVENTION

The invention relates to a connector system with a coupling system and a port system for coupling flexible tubing to a container containing medicinal liquids.

DE-A-197 17 765 describes a sterile connector system for linking flexible tubing to a foil bag or tank containing a medicinal liquid. The known connector system is comprised of a coupler or port system which is equipped with a channel-type cavity and which is sealed by a pierce-through diaphragm. The coupler is comprised of a lower base part that can be welded to the bag and a tubular upper part (connector) for accommodating the puncturing boss (spike), at which the flexible tubing is attached. A sterile connector system as described in the foregoing is also described in DE-A-196 37 856.

The known connector systems have been successful in practical applications. It is a disadvantage, however, that the spike, prior to its connection to the bag, is exposed to the non-sterile environment. Caps or similar contrivances are common as closing elements; however, their disadvantage is the fact that they must be removed before insertion of the spike into the connecter, whereby the spike is unprotected when being inserted.

PCT96/00093 describes a connector system in which the spike is enclosed by a flexible hose which is fastened to the tubular upper part (connector) of the coupler by means of a coupling nut. For the purpose of creating the fluid connection, the spike is screwed into the tubular upper part of the coupler, whereby the diaphragm obturating the upper part is pierced. The disadvantage is that the maximal extensibility and deformability of the hose limits the clearance range of the spike. This is a disadvantage inasmuch as a diaphragm situated deep in the connector and which is sufficiently touch-protected can be penetrated by the spike only if the spike is inserted deeply into the connector, which makes handling more difficult. Moreover, there is the risk that the flexible hose may tear, resulting in system leakage. Furthermore, drawing the flexible hose onto the spike makes the creation of the connector system more difficult. From the point of view of waste management, it is also a disadvantage that the connector is made of different materials.

BRIEF SUMMARY OF THE INVENTION

Therefore the object of the present invention is to provide an easy-to-use and inexpensive connector system that is easy to manufacture and whose spike is adequately touch-protected when being connected to the tank or bag.

This problem is solved by a connector system having a coupling system and a port system constructed according to the principals of the present invention.

A spike of the coupling system of the present invention is enveloped along its entire length by a spike sheath which has a first part and a second part. The first part and the second part can be screwed into each other in order to telescopically elongate or shorten the spike sheath. To accomplish this, the first part can be provided either with an internal threading and the second part with an external threading or the first part with an external threading and the second part with an internal threading. The second part of the spike sheath can be coupled to a connector of the port system.

For coupling the spike to the port system, the spike sheath is connected to the connector of the port system. Then, for shortening the spike sheath axially, the first part is screwed completely onto or into the second part, whereby the spike pierces a diaphragm of the port system and so establishes the fluid connection. In so doing, the spike is protected from contact.

In one preferred embodiment of the invention, the diaphragm is a foil situated on the underside of a base element of the port system. The pierce-through diaphragm can also be a foil situated between the connector and the base element. In lieu of a foil, flat plastic laminate or similar material, which is one piece with the port system, may be used as the diaphragm. The deeper the diaphragm lies, the longer the first part and the second part of the spike sheath must be. Using a diaphragm that is situated higher, the axial length of the spike sheath can thus be shortened. Compact construction with satisfactory touch-protection results if the diaphragm is situated in the middle of the channel-type cavity of the port system.

The second part of the spike sheath is appropriately screwed onto the connector of the port system. In order to screwably attach the second part to the connector, the connector is provided with an external screw thread and the second part is provided with an internal screw thread. In lieu of a screw connection, a bayonet fastening or similar system can be used.

In another preferred embodiment of the invention, the second part of the spike sheath forms a stop for the first part in which the second part consists of two sections with different diameters. For consistent securing of the two parts of the spike sheath, a threaded stop can be provided. In addition, the first part should be fastened securely to the spike.

In order to assure that the spike does not co-rotate on connection to the port system, a guide piece is advantageously provided on the connector and the spike pushed into it to prevent rotation or swiveling.

An alternative embodiment of the connector system eliminates the telescopic extension of the spike sheath. The spike sheath is a union nut which extends beyond the tip of the spike such that the spike is enveloped over its entire length. In this embodiment, the diaphragm is not in the base element or between the insert base element and the connector, but is situated in the connector of the port system, such that the spike can pierce through the diaphragm when the spike sheath is screwed on.

BRIEF DESCRIPTION OF THE DRAWINGS

The embodiments of the invention will be described with greater specificity and clarity with reference to the drawings, in which.

DETAILED DESCRIPTION

The connector system consists of a port system [1] and a coupling system [2], the latter of which is composed of a spike [3] and a spike sheath [4].

The port system [1] made, for example, of injection molded polyethylene includes a floater-like base element [5] with an annular segment [6], which is equipped with two radially extending flanges [7,8], which lie in a common plane. The base element can be incorporated into conventional packaging containing medicinal liquids. The base element can, for example, be welded into foil bags which are filled with internal feeding solutions.

A tubular connector [9] connects to the base element [5] of the port system [1] and is provided with an external screw thread [10] for screwing on the spike sheath [4] of the coupling system [2]. At its uppermost edge, the connector [9] exhibits a circumferential, internally protruding flange [11] that extends into a guide [12] to accommodate the spike [3] of the coupling system [2] to prevent swiveling. The guide [12] exhibits a rectangular cross-section with rounded corners which corresponds to the cross-section of the spike [3].

The channel-type cavity [13] in the base element [5] and the connector [9] is sealed or obturated with a diaphragm or membrane [14]. The diaphragm [14] is a foil welded to the underside of the base element with very minimal oxygen permeability, which extends over almost the entire surface of the base element. A similar port system is specifically described in DE-A-197 17 465 to which express reference is made.

The spike [3] of the coupling system [2] exhibits at its lower end a point [15]; at its upper end the spike is provided with a connector [16] for connection of flexible tubing [17] of a flexible tubing delivery system. The spike [3] seals against the internal guide [12] of the connector [9].

Figure 2:
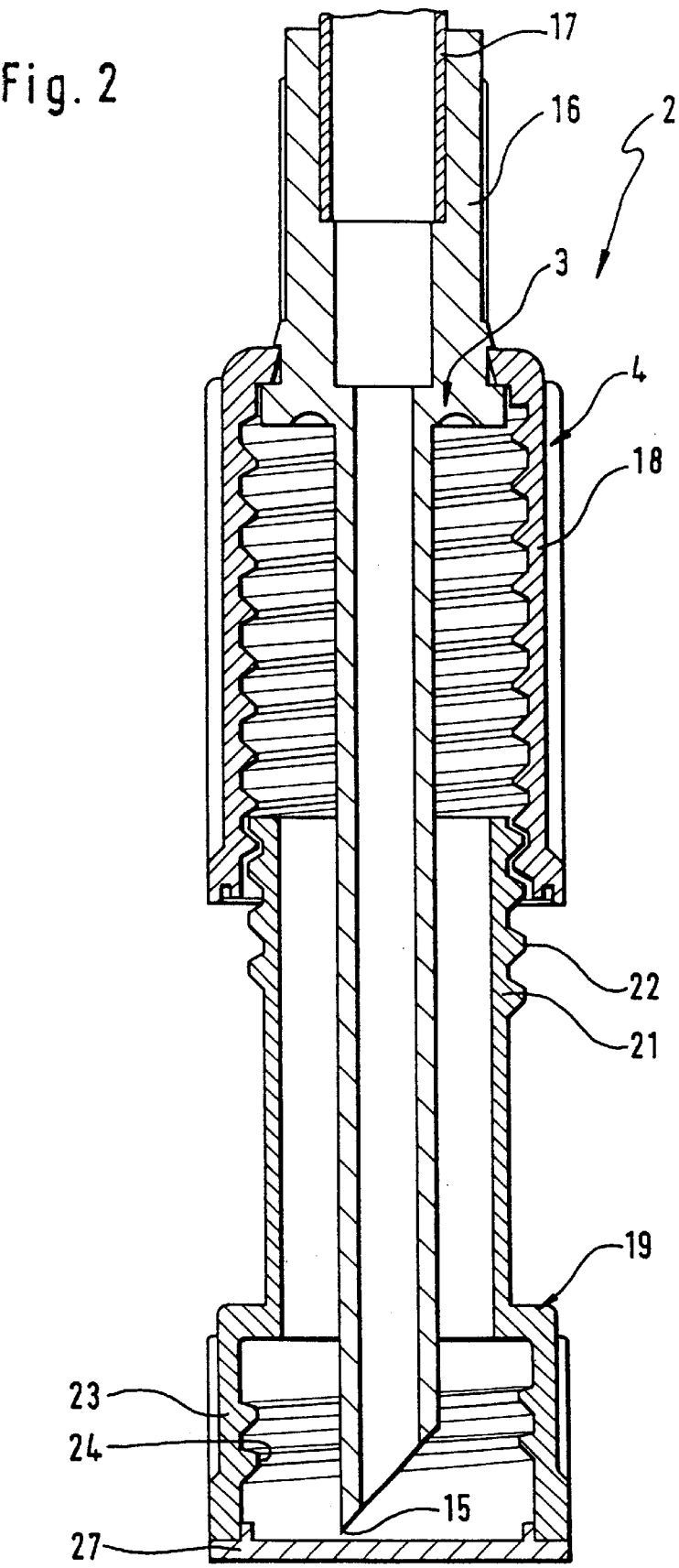
FIG. 2 illustrates the coupling system of the connector system in the cross-sectional representation of FIG. 1.

The spike sheath [4] consists of a first tubular part [18] and a second tubular part [19] that are connected by screwing the one onto the other. The first part [18] of the spike sheath [4] rotates but is securely fastened to the connector [16] of the spike [3]. It extends approximately over half of the length of the spike and has an internal thread [20]. The second part [19] has a first segment [21] having an external thread [22] that can be screwed onto the first part [18] of the spike sheath [4], and a second segment [23] having an internal thread [24], that can be screwed onto the connector [9] of the port system [1]. The second segment [23] of the second part [19] exhibits a larger diameter than the first segment [21] such that the second part forms a stop element for the first part [18] of the spike sheath [4]. The length of the first and second parts of the spike sheath is so dimensioned that the spike is enveloped over its entire length by the spike sheath when the two parts are not completely screwed together. For enhancement of security, the spike sheath [4] is closed or obturated by an additional cap [27] that is inserted into the second part [19] of the spike sheath [4] (FIG. 2).

For connection of the coupling system [2] to the port system [1], the second part [19] of the spike sheath [4] is screwed onto the connector [9] of the port system [1]. When this is done, the second part [19] of the spike sheath [4] abuts an annular flange or stop [26] of the connector [9]. Then the first part [18] is completely screwed onto the second part [19] of the spike sheath [4], whereby the spike [3] advances into the guide [12] of the connector [9] and continues into the channel-type cavity [13] of the port system until it pierces the diaphragm [14]. Thus, a fluid connection is established.

Figure 1:
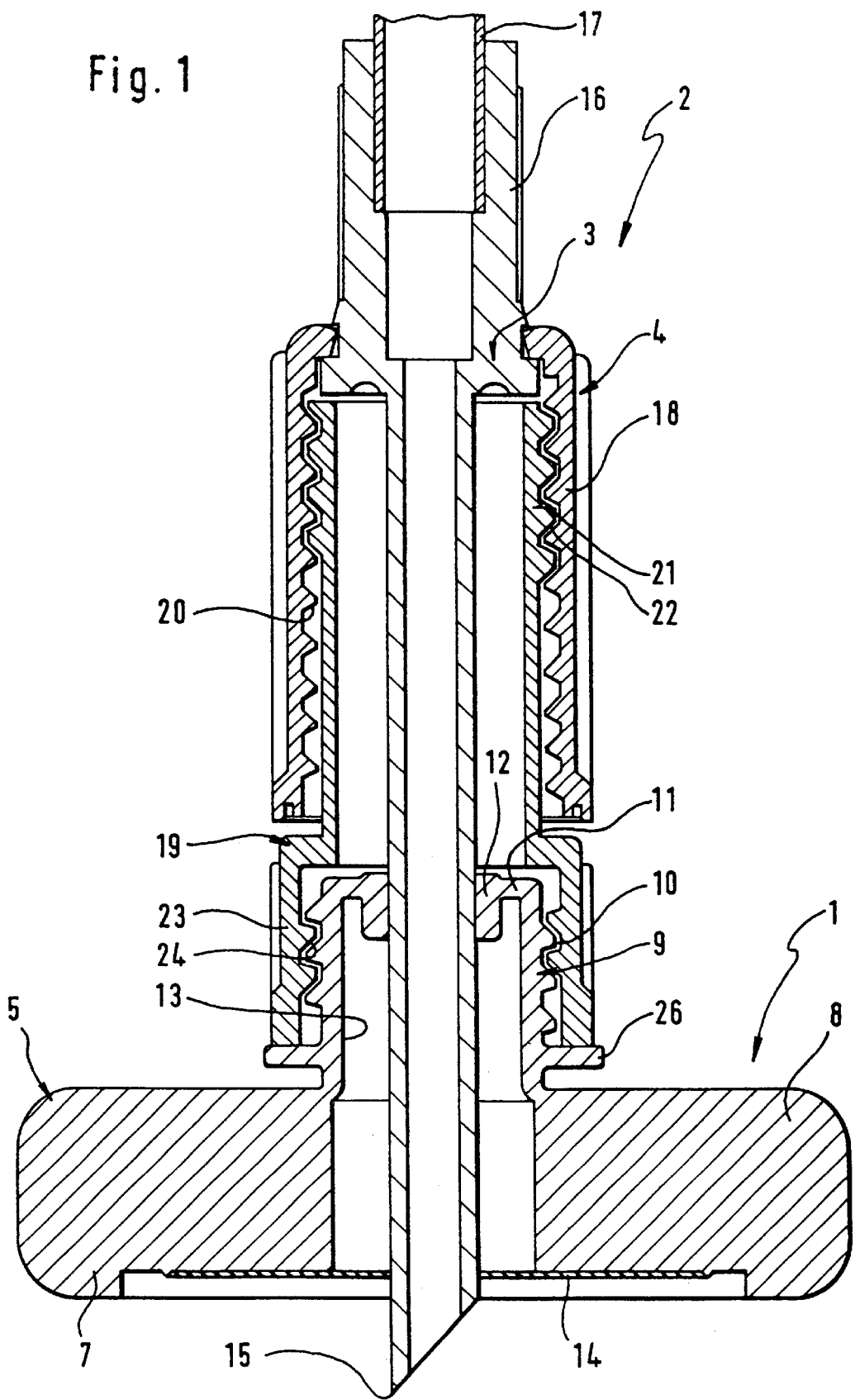
FIG. 1 illustrates a first embodiment of the coupling and port systems of the connector system with a deep-lying diaphragm in cross-sectional view.
Figure 3:
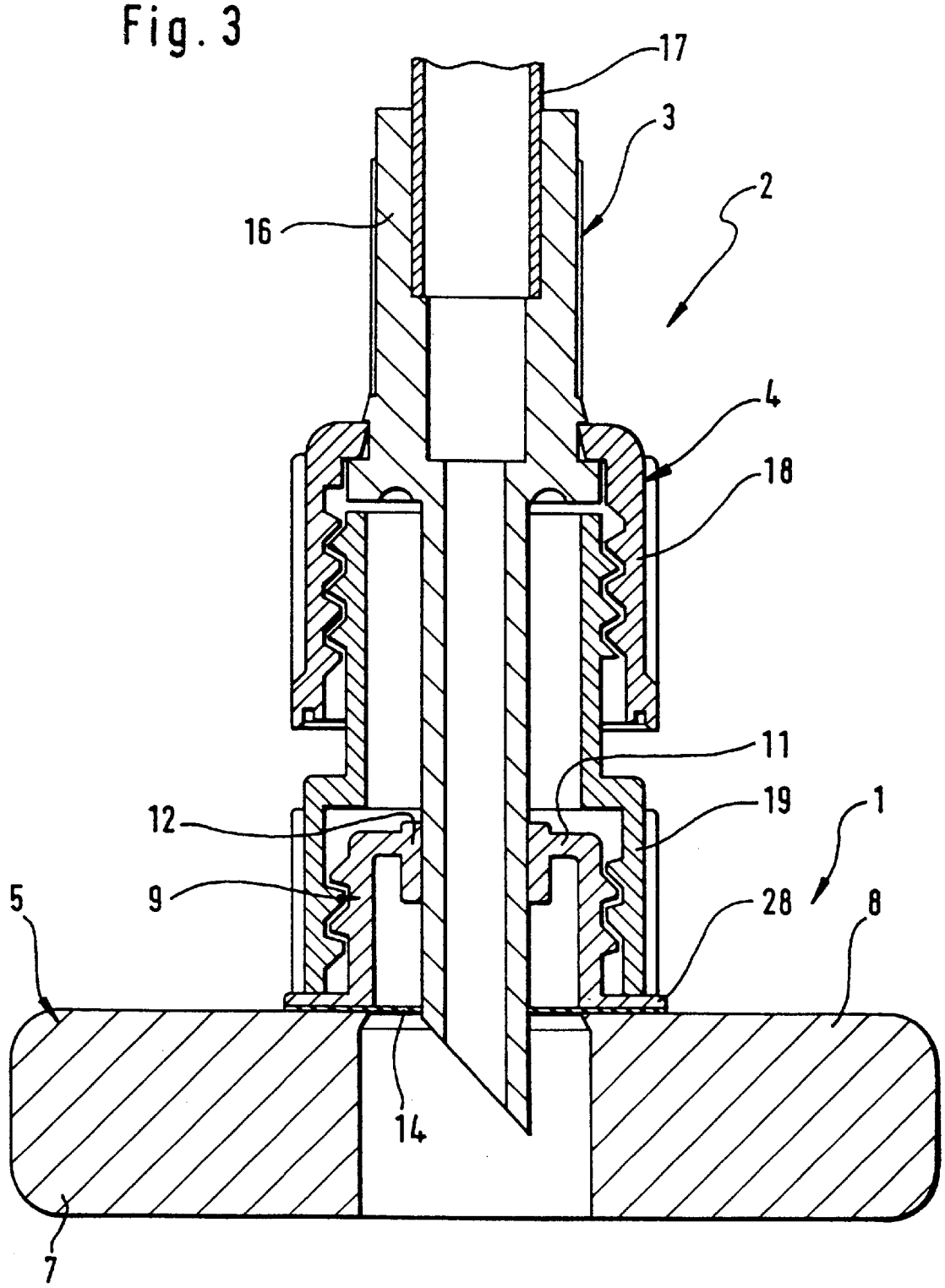
FIG. 3 illustrates a second embodiment of the connector system that exhibits a particularly compact configuration.

FIG. 3 illustrates a further embodiment of the connector system that exhibits a compact configuration. The parts of the embodiment shown in FIG. 3 that correspond to those shown in the embodiments illustrated in FIGS. 1 and 2 are marked with the identical reference numbers. The embodiment shown in FIG. 3 differs from the embodiments shown in FIGS. 1 and 2 merely in that the diaphragm [14] is a foil that is welded to the upper side of the base element [5] of the port system [1] rather than to the under side. In this embodiment, the connector [9] is provided with an annular flange [28] that is welded to the base element [5] Since the diaphragm [14] is raised, the length of the first and second parts [18,19] of the spike sheath [4] can be shortened, whereby the connector system assumes a compact configuration.

Figure 4:
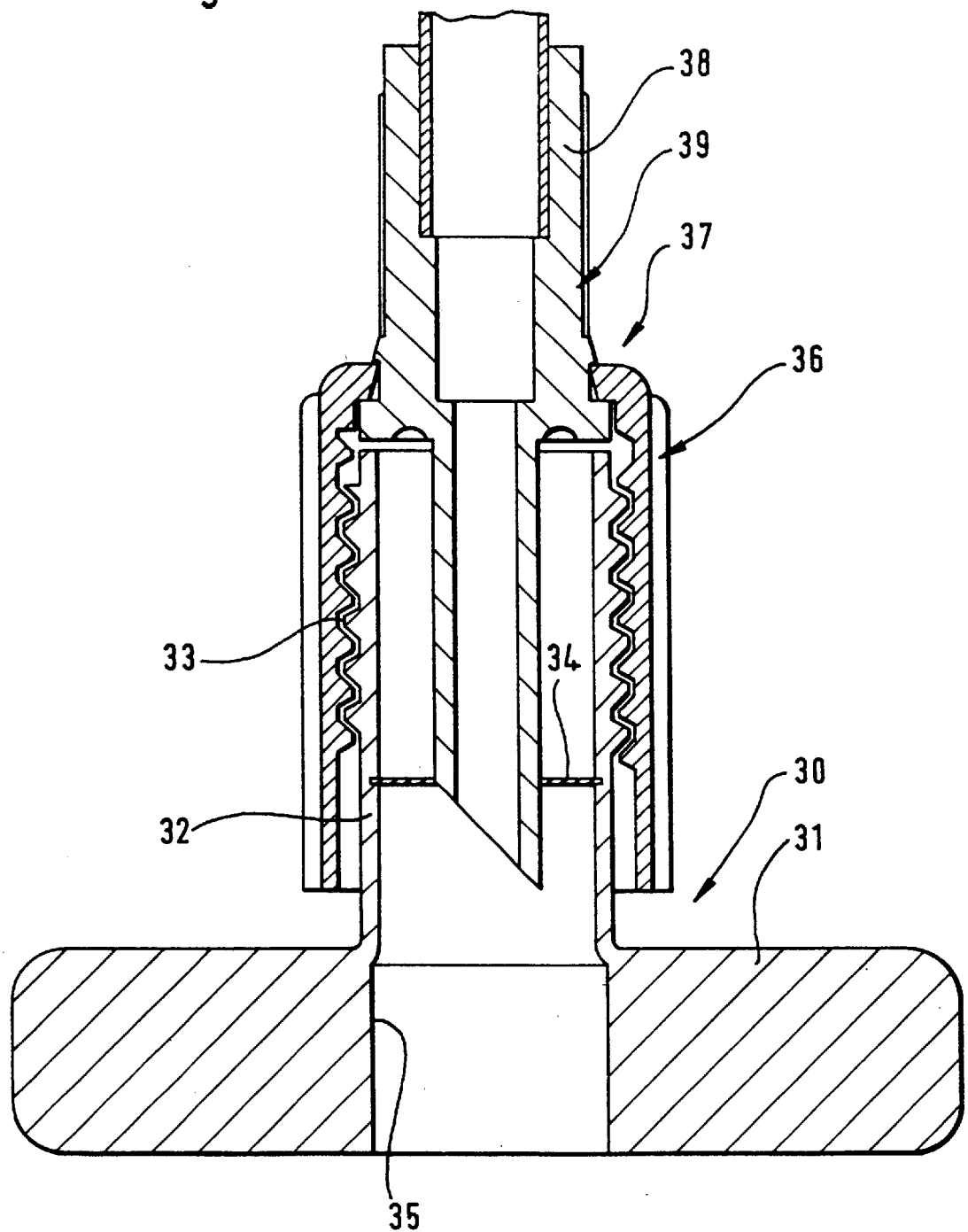
FIG. 4 illustrates a third embodiment of the connector system in cross-sectional representation, whose spike sheath is not extendable telescopically.

FIG. 4 illustrates an embodiment of a connector system exhibiting a simplified configuration that differs from those described in the foregoing embodiments in that the spike sheath cannot be extended telescopically. The port system [30] of the connector system exhibits a base element [31] with a tubular connector [32] that is provided with an external thread [33]. The diaphragm [34] that seals the channel-type conduit [35] of the port system [30] is situated in the lower half of the connector [32]. The diaphragm [34] can be an injection molded piece inserted into the connector or can be injection molded in one piece with the connector. The spike sheath [36] of the coupling system [37] is a union nut, which is secured unremovably on the connector [38] of the spike [39]. It extends over the entire length of the spike.

For connecting the coupling system [37] to the port system [30], the union nut [36] is screwed onto the connector [32], whereby the spike [39] is advanced into the connector [32] and the diaphragm [34] is pierced. Thus, the fluid connection is established.

What is claimed is:

1. A connector system having a coupling system and a separate port system for coupling a flexible tubing system to a container containing medicinal liquid, wherein:
    the coupling system comprises a spike connectible to the flexible tubing system, and a spike sheath enveloping an entire length of the spike;
    the port system includes a base element insertable into the container and an externally threaded tubular connector extending from said base element, the base element having a channel-type cavity that continues into the connector, and the channel-type cavity is obturated with a pierceable diaphragm; and
    the spike sheath of the coupling system has a first part and a second part that can be screwed together for elongation or shortening, and the second part has an internal thread such that the spike sheath can be screwed onto the connector of the port system.

2. A connector system as recited in claim 1, wherein the pierceable diaphragm is a foil situated on a side of the base element distal to the connector.

3. A connector system as recited in claim 1, wherein the pierceable diaphragm is a foil situated between the connector and the base element.

4. A connector system as recited in claim 3, wherein the first part of the spike sheath comprises a union nut with internal threading and the second part has an external thread such that the first part can be screwed onto the second part.

5. A connector system as recited in claim 4, wherein the second part of the spike sheath has a first segment with a first diameter and a second segment with a second diameter larger than the first diameter such that the second part forms a stop element for the first part.

6. A connector system as recited in claim 1, wherein the first part of the spike sheath is fastened to the spike and rotatable relative to the spike.

7. A connector system having a coupling system and a separate port system for coupling a flexible tubing system to a container containing medicinal liquid, wherein:

the coupling system comprises a spike connectible to the flexible tubing system, and a spike sheath enveloping an entire length of the spike;

the port system includes a base element insertable into the container and a connector extending from said base element, the base element having a channel-type cavity that continues into the connector, and the channel-type cavity is obturated with a pierceable diaphragm; and the spike sheath of the coupling system has a first part and a second part that can be screwed together for elongation or shortening, the second part is connectable to the connector of the port system, the first part of the spike sheath is fastened to the spike and rotatable relative to the spike, and the connector further includes a guide having a through opening for receiving and preventing rotation of the spike.

8. A connector system having a coupling system and a separate port system for coupling a flexible tubing system to a container containing medicinal fluids, wherein:

the port system includes a base element insertable into the container and a threaded tubular connector extending from said base element, said base element having a channel-type cavity that continues into a the connector, and wherein the channel-type cavity is obturated with a pierceable diaphragm, and the coupling system comprises a spike connectable to a tube inlet of the flexible tubing system, and a single union nut screwable onto the connector, wherein the union nut is configured as a sheath enveloping an entire length of the spike and the diaphragm is situated in such a manner in the connector, that it is pierced when the union nut is screwed onto the connector for establishing a fluid connection.

9. A connector system as recited in claim 8, wherein the union nut is fastened unremovably to the spike.

10. The connector system as recited in claim 8 wherein the opening of the guide has a rectangular cross-section with rounded corners corresponding to a cross-section of the spike.

* * * * *